United States Patent
Gormley et al.

(10) Patent No.: US 10,406,095 B2
(45) Date of Patent: Sep. 10, 2019

(54) COMPOSITIONS AND METHODS FOR PROTECTING BLEACHED HAIR AND ENHANCED OXIDATIVE HAIR COLORING

(71) Applicant: Grant Industries, Inc., Elmwood Park, NJ (US)

(72) Inventors: John Gormley, Midland Park, NJ (US); Ronald V. Lerum, Elmwood Park, NJ (US); Juan Carlos Salgado Quintanilla, Bellavista (PE)

(73) Assignee: GRANT INDUSTRIES, INC., Elmwood Park, NJ (US)

( * ) Notice: Subject to any disclaimer, the term of this patent is extended or adjusted under 35 U.S.C. 154(b) by 0 days.

(21) Appl. No.: 16/044,760

(22) Filed: Jul. 25, 2018

(65) Prior Publication Data

US 2019/0083380 A1 Mar. 21, 2019

Related U.S. Application Data

(60) Provisional application No. 62/559,169, filed on Sep. 15, 2017.

(51) Int. Cl.
| | |
|---|---|
| *A61K 8/898* | (2006.01) |
| *A61K 8/34* | (2006.01) |
| *A61K 8/362* | (2006.01) |
| *A61K 8/41* | (2006.01) |
| *A61K 8/22* | (2006.01) |
| *A61K 8/25* | (2006.01) |
| *A61Q 5/08* | (2006.01) |
| *A61Q 5/00* | (2006.01) |
| *A61K 8/23* | (2006.01) |
| *A61Q 5/10* | (2006.01) |
| *A61K 8/899* | (2006.01) |

(52) U.S. Cl.
CPC .............. *A61K 8/898* (2013.01); *A61K 8/22* (2013.01); *A61K 8/23* (2013.01); *A61K 8/25* (2013.01); *A61K 8/345* (2013.01); *A61K 8/362* (2013.01); *A61K 8/41* (2013.01); *A61K 8/899* (2013.01); *A61Q 5/002* (2013.01); *A61Q 5/004* (2013.01); *A61Q 5/08* (2013.01); *A61Q 5/10* (2013.01); *A61K 2800/4324* (2013.01); *A61K 2800/882* (2013.01)

(58) Field of Classification Search
CPC ...................................... A61K 8/898
See application file for complete search history.

(56) References Cited

U.S. PATENT DOCUMENTS

| | | |
|---|---|---|
| 3,193,464 A | 7/1965 | Edman et al. |
| 5,596,061 A | 1/1997 | Berger et al. |
| 5,641,478 A | 6/1997 | Syed et al. |
| 6,124,490 A | 9/2000 | Gormley et al. |
| 6,440,177 B1 | 8/2002 | Orr |
| 6,730,765 B1 | 5/2004 | Roth |
| 7,566,348 B2 | 7/2009 | Narasimhan et al. |
| 8,053,513 B2 | 11/2011 | Gormley et al. |
| 8,952,080 B2 | 2/2015 | Jan |
| 9,095,518 B2 | 8/2015 | Pressly et al. |
| 9,326,926 B2 | 5/2016 | Pressly et al. |
| 9,498,419 B2 | 11/2016 | Pressly et al. |
| 2015/0034117 A1 | 2/2015 | Pressly et al. |
| 2015/0037271 A1 | 2/2015 | Pressly et al. |
| 2016/0206535 A1 | 7/2016 | Pressly et al. |

*Primary Examiner* — Benjamin J Packard
(74) *Attorney, Agent, or Firm* — Lucas & Mercanti, LLP

(57) ABSTRACT

Compositions and methods useful for maintaining the structural integrity of keratin in the presence of hair bleaching agents and coloring dyes are disclosed. The compositions provide a significant improvement in minimizing hair breakage while improving hair conditioning, smoothness and styling.

34 Claims, No Drawings

COMPOSITIONS AND METHODS FOR PROTECTING BLEACHED HAIR AND ENHANCED OXIDATIVE HAIR COLORING

CROSS-REFERENCE TO RELATED APPLICATIONS

This application claims the benefit of priority from U.S. Provisional Patent Application Ser. No. 62/559,169 filed Sep. 15, 2017, the contents of which are incorporated herein by reference.

FIELD OF THE INVENTION

This invention pertains to hair coloring treatment methods and formulations applied during the beaching process. Color treatments include hair coloring, highlighting, and bleaching. The invention, in particular, relates to compositions and methods for improving hair integrity during hair damaging conditions.

BACKGROUND OF THE INVENTION

The structure of hair and chemistry assist in defining the parameters needed to strengthen the hair during the bleaching process and color treatment. The hair structure is composed of the cuticle, cortex and medulla. The cuticle is the outer protective layer of the hair fiber, which provide the sensory and shine characteristics of hair. The cuticles physically overlap, thereby forming a shield like barrier to protect the hair from chemical, physical and environmental treatments. The cortex is the major component of the hair and is responsible for the mechanical strength. The inner most of the hair fiber is the medulla and contains much of the melanosomes, which provide hair its pigment color.

The chemistry of hair is what provides and maintains hair its structural integrity. The hair is primarily composed of proteins, lipids and water. Human hair is composed of 65-95% protein, which gives hair much of its properties, such as curly, wavy, kinky, straightness, etc. The composition of lipids in hair is 1-9%, enhancing the conditioning properties, such as flexibility, surface gloss and lubricity of hair. Lipids in the internal part of the hair provide structural reinforcement and rigidity. Water is another major component of hair. The water forms strong hydrogen bonds with proteins, thereby influencing the tensile strength, swelling, flexibility and shape of hair.

Hair bleaching requires one or more cycles of applying high concentrations of bleaching agent to permanently decolor the hair by oxidizing melanin in the cortex of the hair. The bleaching process is often highly alkaline (pH 10-13) resulting in a dramatic degradation of the structural integrity of the hair. Several products are commercially available that are promoted to enhance the quality of the hair when added to the bleaching process. For instance, US 20160206535 A1, U.S. Pat. No. 9,326,926 B2 discloses formulations, kits, and methods for rebuilding the disulfide bonds in keratin found in hair, skin, or nails. U.S. Pat. No. 9,498,419 relies on maleic acid. US2015/0034117A1 relies on maleic acid and ionic linkers that as described are preferably water soluble. Hydrophobic siloxanes are not mentioned as a possible linker in any above referenced prior art.

Hair that is damaged due to a hair coloring treatment and/or other reducing treatment, such as during a permanent wave, can be treated with the formulations containing one or more active agents. The formulations may be applied after a hair coloring treatment or simultaneously with a hair coloring treatment. Use of the active agent formulations during a permanent wave treatment prevents the reversion of the hair to its previous state for extended periods of time. The above referenced patent family discusses use of maleic acid and its salts, formulated into aqueous media. This class of ingredient is very hydrophilic and while having some activity, it is not fully reacted during the bleaching cycle, and the remainder would wash out of the hair rapidly during subsequent processing and washing.

Similar damage to the hair can also result from permanent wave treatments. In both coloring and permanent wave processes, improvements are also needed to repair damage and/or to strengthen the hair during or after such styling treatments. Additionally, improved treatments and methods are needed which can be applied to skin and nails to repair damaged keratin.

Maleic acid is commonly used as a neutralizer in cosmetic applications, however the percentage presumably used in bleaching applications would be significantly higher, most likely greater than 5% and would be outside the recommended use level reviewed by the expert panel [Int J Toxicol. 2007; 26 Suppl 2:125-30 Final report on the safety assessment of Maleic Acid.] In this cosmetic ingredient review, expert panelists discussed a study of 50 human subjects wherein maleic acid at 20% was applied to one forearm daily for a period of 6 weeks. Acute vesicular dermatitis was observed in 17 subjects, who were dropped from the study. Only five of the remaining subjects accommodated to the treatment, the rest had varying degrees of inflammation or hyperirritable skin. Although maleic acid itself may be a dermal and/or ocular irritant, its use as a pH adjustor in cosmetic formulations dictates that most of the acid will be neutralized into various maleate salts. The claims in U.S. Pat. No. 9,326,926 include the use of the free acid at a level which would be outside of the scope of the expert panel's recommendations for reviewed safe use. In cases when the maleic salts are used, the bleaching process includes neutralization steps that may incidentally create high exposure to free maleic acid which is an irritant.

U.S. Pat. No. 5,641,478 discusses the use of a cationic polymer for strengthening hair while applying the hair swelling component. This allows the cationic polymer to be affixed to the hair.

U.S. Pat. No. 6,124,490 discloses ionically cross-linked polymers that were potent thickeners that contained a PCA group paired with a secondary amine together on the same pendant group. The position could be anywhere on the molecule including the terminus of the polymer on either side or both sides. The zwitterionic nature is distinctive from a PCA group without the paired amine.

U.S. Pat. No. 8,053,513 teaches that with adding a higher degree of PCA groups, the more hydrophilic the product can become, even becoming water soluble and detergent like. For instance, the properties of 2-pyrrolidone-4-carboxylic acid substituted polysiloxanes can be dramatically altered by increasing the presence of the carboxylic acid-substituted pyrrolidone monomers on the polysiloxane. This results in enhanced detergent and solubility in water and the ability to form water-in-oil emulsions thereby providing usefulness across a broad range of formulations having enhanced electrolytic and silicone and/or hydrocarbon compatibility and cleansing properties. The general polymers described by U.S. Pat. No. 8,053,513 B2 and other related prior art are pendant-functional materials containing one or more PCA groups. The authors made no provision for PCA groups exclusively residing at the alpha-omega terminal ends of the molecule.

U.S. Pat. No. 6,730,765 B1 discloses a method for the preparation of reacting maleic anhydride with a bis-amino siloxane resulting in at least a mono-functional maleamic functionalized silicone and is also suitable for use in this invention. A similar polymer was made in accordance to U.S. Pat. No. 8,952,080, [specifically example 2 Preparation of Siloxane Macromer (B) exhibited as their structure V].

SUMMARY OF THE INVENTION

The invention relates to compositions and methods for improving hair integrity during hair damaging conditions, such as bleaching process and color treatment. In the past, the end result of the processes extensively damages both the structure and chemistry of the hair that becomes typically dry and straw-like, frizzy, difficult to style and easily broken. Hair lacks regenerative properties because it is dead on a cellular level. Therefore, it is important to introduce components during the bleaching and color treatment processes that maintain and/or enhance the hair's structural integrity and chemistry.

Therefore, it is an object of this invention to provide improved formulations and methods for repairing and/or strengthening damaged hair that do not rely on free maleic acid and/or their salts. The formulations and methods of repair and/or strengthening hair are applied during the process in which hair is chemically treated, thereby allowing the product to deposit and penetrate into the cortex of the hair as well as the cuticle with no loss of product. The compositions and methods also enhance the saturation of oxidative hair colors, while sealing the color treatment for improved color fastness, and protecting the structural integrity during concurrent oxidative bleaching, thus improving the appearance and texture of colored hair. The formulations are preferably applied during the hair coloring process without the need of a pretreatment step.

In one aspect of the invention there are provided hair treatment compositions containing
a) from about 1% to 25% by weight of a polymer of Formula (I):

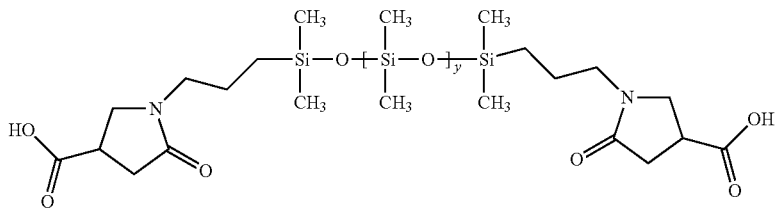

Bis-PCA Dimethicone Structure or Formula (II)

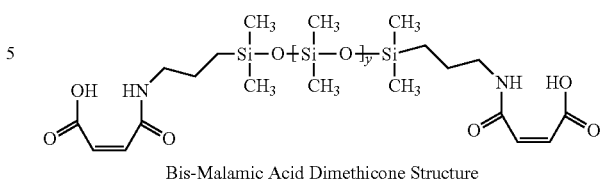

Bis-Malamic Acid Dimethicone Structure wherein y is 6 to 20;
b) from about 0.1 to 10% by weight of a surfactant;
c) from about 5 to about 30% by weight of a humectant;
d) a pH adjuster in an amount sufficient to bring the pH of the hair treatment composition to from about 9 to about 10; and
e) water;
wherein the hair treatment composition is substantially free of maleic acid.

Another object of the invention is to provide a bleaching formulation comprising a hydrophobic active agent capable of forming a protective complex within the hair that does not wash away and does not prevent effective bleaching in terms of color saturation, color development, color consistency, improved wash resistance, and improved hair conditioning when applying color treatments. The nature of the chemical color process should remain consistent before and after UV exposure.

A further object of the invention is to provide compositions and methods for improving hair color saturation. As such, the compositions containing the bis-PCA Dimethicone polymers described herein are applied to hair in combination with hair dye compositions. For example, during the oxidative hair coloring process, consumers desire enhanced color deposition, color fastness, enhanced color vibrancy and intensity. The hair coloring process itself can lead to poor color deposition, therefore not producing the expected color vibrancy. In addition, the hair appears straw-like, dry and fragile. The process during the hair coloring product involves the use of a developer and alkalizing agent. The developer is usually an oxidizing agent, such as, hydrogen peroxide in water, cream or lotion. Hydrogen peroxide is the typical catalyst that promotes the reaction of the hair coloring dyes. The alkalizing agent is most often ammonia or alkaline bases. These alkaline conditions allow hair to swell and allow the pigment to penetrate the hair cuticle.

It is important to allow the pigment to penetrate deep and exchange with natural melanin. Accordingly, a simple, consumer friendly, additive is desired to alleviate the frustrations due to the hair coloring process. The compositions and methods of the invention address this need in the field of hair coloring and enhance color deposition and color fastness, while leaving the hair fiber with the appearance of healthy, smooth and silky hair. Since bleaching and oxidative hair coloring both use hydrogen peroxide, it is a further object to improve relative the structural integrity after such treatment by using the compositions on the hair when such treatments are being applied to the hair. The inventive compositions can also be applied to previously bleached and colored hair to achieve the beneficial effects. Consumers with noticeable signs of early gray hair can also apply the compositions to achieve beneficial results.

In accordance with these objects and further aspects of the invention there are provided hair compositions, bleaching compositions, and combination hair bleaching and coloring/dyeing compositions, all including the bis-PCA dimethicone polymer or the containing hair treatment compositions described above the bis-PCA dimethicone. Methods of treating hair using the compositions and kits containing the compositions described herein as well as kits having a plurality of containers for individually holding the bis-PCA dimethicone hair compositions, hair bleaching and/or hair dyeing compositions are also provided.

DETAILED DESCRIPTION OF THE INVENTION

The hair product solution can be seen as a damage preventing formula which is aqueous and easily mixed with typical hair bleaching or hair coloring treatments with no interference in the viscosity of the finish formula. The compositions described here are useful for maintaining the structural integrity of hair and its components, such as keratin, in the presence of hair bleaching agents. The compositions also improve hair conditioning, smoothness and styling.

Silicones or polysiloxanes are generally non-toxic, non-irritating liquid polymeric molecules exhibiting good heat stability and chemical resistance against oxidation and reduction. This class of molecules range from very short polymer length or low molecular weight varieties to long chain polymers that are viscous gums. The most commonly used commercial class is polydimethylsiloxane where all alkyl groups are methyl. Such methyl groups can be substituted with longer alkyl chains or many other functional chemical groups as known to those skilled in the art. A pyrrolidone carboxylic acid (PCA group) such as 2-pyrrolidone-4-carboxylic is one possible substitution and forms an anionic functional group upon being neutralized by a base such that a degree of hydrophobicity is adjusted for any particular polymer. U.S. Pat. No. 5,596,061 disclosed the first synthesis of this molecule. The PCA group can be located at any position, including one or both terminal positions on the molecule. A molecule with both terminal positions containing the PCA structure is hereby defined as bis-PCA-Dimethicone.

Example ligand 2-pyrrolidone-4-carboxylic functional group which is linked to the siloxane.

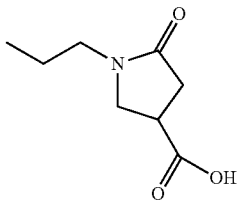

In this invention, a bis-PCA-Dimethicone molecule was specifically synthesized to a medium degree of polymerization such that it remained hydrophobic and is generally water insoluble even when neutralized. Likewise, a bis-maleamic acid dimethicone may also be employed as long as it is essentially water insoluble even after neutralization. Otherwise, formulation stability may be obtained by the combination of amine bases, co-solvents (like polyols, and glycols), surfactants and/or additives. Bis-PCA Dimethicone is synthesized from itaconic acid reacted onto both terminal positions using an alpha-omega-aminopropyl-polydimethylsiloxane in a condensation reaction as published in U.S. Pat. No. 5,596,061.

While not being bound to theory, we believe the polymer ends are fully ionized and capable of forming a strong ionic bond with amines in the keratin structure, particularly those amines found on the ends of damaged hair sections. This ionic bond is especially useful in preventing further hair damage when the PCA Dimethicone is co-formulated with volatile amines and other solubilizing agents that favor the exchange of volatile amine with the amino group in the hair. After the volatile amines are exchanged, the hydrophobicity of the modified silicone increases and remains after rinsing as a coacervated phase. Among others, common amines capable of being exchanged are aminomethyl propanol (AMP-95) and triethanolamine (TEA). In addition to forming strong ionic bonds with the proteins in hair, the PCA can form hydrogen bonds with water. Maintaining the hydration of hair is essential to healthy hair. The dimethicone has the ability to coat the surface of the hair, thereby exchanging the lipids lost during the treatment cycles. The dimethicone deposited on the hair maintains the surface hydrophobicity and the hair's conditioning behavior.

In accordance with one aspect of the invention there are provided hair treatment compositions, comprising a) from about 1% to 25% by weight of a polymer selected from Formula (I):

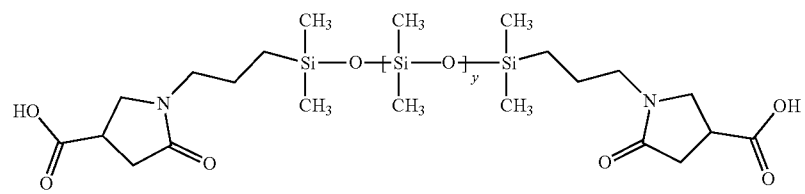

Bis-PCA Dimethicone Structure or Formula (II)

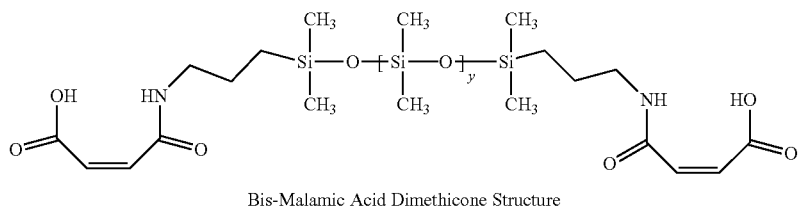

Bis-Malamic Acid Dimethicone Structure wherein y is 6 to 20;
b) from about 0.1 to 10% by weight of a surfactant;
c) from about 5 to about 30% by weight of a humectant;
d) a pH adjuster in an amount sufficient to bring the pH of the hair treatment composition to from about 9 to about 10; and
e) water;
wherein the hair treatment composition is substantially free of maleic acid.

For purposes of the present invention, "substantially free" shall be understood to mean compositions having less than about 0.1% by weight maleic acid.

In some preferred aspects of the invention the amount of the polymer is from about 15 to about 20% by weight. In other aspects y is an integer of from 8 to 12, and preferably is 10. In other aspects, the compositions preferably include the bis-PCA dimethicone compound of Formula (I).

Other cosmetic ingredients may be incorporated in the inventive compositions such as plant extracts, vitamins, minerals, anti-oxidants, scalp conditioning agent(s), such as humectants and emollients; alcohols, fats and oils, surfactants, fatty acids, silicone oils, thickeners, viscosity modifiers, emulsifiers, stabilizers, coloring agents, preservative, chelating agents, film formers, fragrances, or any combinations thereof.

Humectants

Humectants include polyhydric alcohols for moisturizing, reducing scaling and stimulating removal of built-up scale from the skin and scalp. Typical polyhydric alcohols include polyalkylene glycols, alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Humectants are used at about a 5 to about 30% by weight range in the inventive compositions with amounts of from about 20 to about 28% by weight in some preferred aspects.

Surfactants

A surfactant is a surface-active compound used to lower the surface tension of water thereby allowing hydrophobic compounds to be more compatible in water. Surfactants have the ability to enhance the deposition of compounds on the surface of hair and can be a co-solvent. One may use a surfactant to enhance the stability of a composition and help form a stable solution or dispersion. Generally, any surfactant category may be used in this capacity. Silicone surfactants are preferred as they form the best interaction with a silicone polymer like bis-PCA-dimethicone. Alkyl dimethicone copolyol type are silicone surfactants and are preferred. More preferred is disodium PEG-12 dimethicone sulfosuccinate, available commercially as Gransurf GR-50 (Grant Inc., Elmwood Park, N.J.). Surfactants are used between from about 1 to about 10% by weight in compositions of the invention with amounts of from about 2 to about 7% by weight in some alternative preferred embodiments.

As mentioned above, the compositions include a pH adjuster so that the compositions the composition have a pH of from about 9.0 to about 10.0. The pH may also be adjusted by including an optional volatile amine pH adjuster such as aminomethyl propanol or triethanolamine.

Volatile amine neutralizers are used, including but not limited to ammonia hydroxide, triethanol amine (TEA), and 2-amino-2-methyl-1-propanol (Angus Chemical AMP-95). Quantities are sufficient to neutralize any ionic polymers and finish at a pH of about 9-12 and in some aspects, a pH range of about 9-10.

The preferred solvent is water but lower aliphatic alcohols including ethanol can be used. Other cosmetically acceptable solvents can be used, including glycols and silicones.

A further aspect of the invention includes hair bleaching compositions which are substantially free of maleic acid and contain (a) from about 1.0 to about 50% by weight of the bis-PCA dimethicone or bis-maleamic acid dimethicone-based hair treatment composition described above and (b) from about 1.0 to about 50% by weight of a bleaching composition containing a peroxide developer and a bleaching base.

Suitable peroxide developers include for example hydrogen peroxide or other compounds known to those of ordinary skill. Suitable bleaching bases can include, for example, mixtures of ammonium persulfate and potassium persulfate.

In one embodiment of the hair bleaching compositions described herein there are provided compositions which further include a permanent hair coloring dye as such dyes are known to those of ordinary skill. The ratio of the hair treatment composition containing the bis-PCA dimethicone or bis-maleamic acid to the permanent hair coloring dye is from about 0.025 to about 0.25:1.

The invention further includes methods of bleaching hair wherein the following steps are carried out:
(a) applying the hair bleaching composition described above to hair for a time sufficient to lighten the hair in color or until the color lightening caused by the applying of the hair bleaching composition is substantially exhausted;
(b) rinsing the hair to substantially remove the alkaline bleaching composition therefrom; and optionally
(c) repeating steps (a), (b) and (c) up to three times to achieve a desired lighter hair color.

The method may further include applying a neutralizer conditioner solution to the hair after steps (b) or (c) for a time sufficient to substantially eliminate any residual alkalinity.

A related aspect of the invention includes methods of maintaining structural integrity of hair during bleaching or dyeing of the hair. These methods include applying to the hair an effective amount of a polymer of Formula (I):

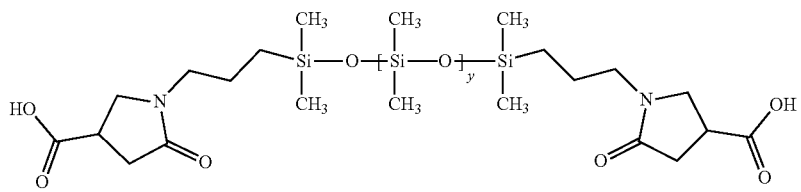

Bis-PCA Dimethicone Structure or Formula (II)

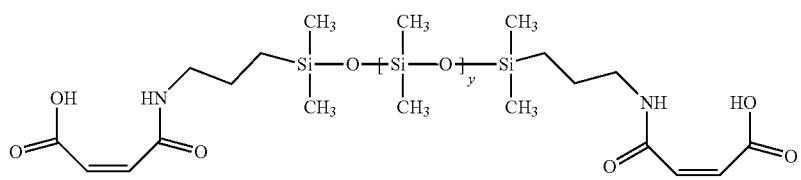

Bis-Malamic Acid Dimethicone Structure wherein y is 6 to 20; in combination with a hair bleaching agent and/or a hair coloring agent.

In a related method there is provided a process of oxidatively dyeing hair while at the same time avoiding damage to the hair to maintain structural integrity of keratin in the hair. The method includes the steps of:
a) applying a permanent hair color dye composition to the hair;
b) applying an oxidizing developer to the hair to catalyze the oxidative dyeing process; and
c) applying to the hair a polymer of Formula (I):

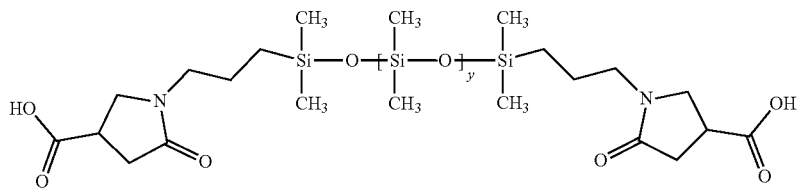

Bis-PCA Dimethicone Structure or Formula (II)

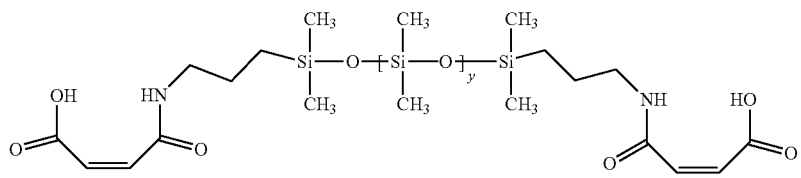

Bis-Malamic Acid Dimethicone Structure wherein y is 6 to 20;
in an amount effective to maintain the structural integrity of keratin in the hair during the oxidative hair dyeing. The permanent hair color dye, the developer and the compound of the Formula (I) or (II) are each applied to the hair for from about 5 to about 60 minutes, to produce a desired shade of color in the hair. If desired, the permanent hair color dye composition of step (a) and the oxidizing developer applied of step (b) are first mixed together before being applied to the hair. An advantage of the methods described herein is that they are carried out with compositions and/or polymers which are substantially free of maleic acid.

Kits are yet another aspect of the invention. The kits include one or more containers having therein at least the protective polymer, i.e. bis-PCA dimethicone or bis-maleamic acid dimethicone and optionally instructions for use of the compositions included therewith. In one kit there is a first container comprising the polymer-containing composition described herein, a second container comprising a hair bleaching composition containing a peroxide developer and a bleaching base, and optionally a third container comprising a hair coloring dye composition.

A hair bleaching process is illustrated in U.S. Pat. No. 3,193,464A, which teaches a hair bleaching composition and method. Bleaching application is a combination of bleach base and hydrogen peroxide developer in the ratio of about two parts of peroxide to each part of base. The peroxide developer, for example 20 volumes, is available in retail and professional supply shops, and bleaches hair most effectively in an alkaline medium. Many alkaline materials have been used, but ammonia is the most effective reagent for activating the peroxide.

Commercially available bleach base is a powder or liquid and may be comprised of a combination of additives to improve performance. Soaps such as ammonium oleate, laurate and stearate, and humectants, such as propylene glycol and glycerin are often included in the formula. Solvents such as the lower alcohols and thickening agents, such as fatty acid amides, ammonia and amines are often included. The usage ratio is sufficient to neutralize the fatty acid and to provide a slight excess of free ammonia to activate the bleaching actions and to adjust the pH to a range of from about pH 9 to about pH 9.7. Additionally, sequestering agents such as salts of ethylenediamine tetra-acetic acid and/or polyphosphates are utilized as well metal complexes as azo dye chelating agent.

Bleach viscosity plays an important role in the application of bleach to the hair. While the bleaching action is independent of the consistency of the composition, it is difficult in practice for an operator to control the application of water-thin bleach, particularly when only portions of the hair are to be lightened. The preferred consistency is one sufficient to maintain its applied locale without running and dripping.

State of the art peroxide and bleach bases, when combined, produce an increased viscosity relative to the bleach base alone, virtually to the point of a gel. It is therefore, of interest to ensure that any addition of an inventive protecting formula to the bleaching/peroxide gel does not affect the bleaching performance as to inhibit the bleaching process or decrease the viscosity of the gel. The composition of the inventive protecting formula was specifically tuned to have enhanced compatibility with the bleaching/peroxide gel.

A bleaching base can be a powder (booster) and is commonly used to obtain a lighter blonde shade, where said booster provides an additional source of bleach; i.e. a mixture of ammonium persulfate and potassium persulfate, sodium metasilicate; peroxide stabilizer, such as a heavy metal sequestrant; anti-caking agent, such as a silica; thickening agents, such as cetyl, or lauryl alcohol; and urea. Bleaching powder treatments are formulas at alkaline pH.

The hydrogen peroxide is typically supplied as a cream emulsion to have compatibility with the bleaching powder or liquid bleaching base. Depending on the desired level of hair color removal or hair color treatment, it will be dependent on the operator to use the level of hydrogen peroxide (such as 10 v, 20 v, 30 v, 40 v, 50 v). V is Volume and is the amount of oxygen that is contained in a given amount of peroxide. For example, 3% hydrogen peroxide is10V, because it will release 10 times it's volume in oxygen. One pint of 3% hydrogen peroxide will release 10 pints of oxygen as it breaks down.

| Developer | H2O2 PERCENTAGE |
|---|---|
| 10 volume or 10V | 3% |
| 20 volume or 20V | 6% |
| 30 volume or 30V | 9% |
| 40 volume or 40V | 12% |

After final rinsing, an optional neutralizer conditioner solution may be applied to completely neutralize any residual alkalinity, whereby said neutralizer solution is slightly acidic buffer solution as commonly sold in salon supply stores under various brand names.

The bis-PCA-dimethicone molecule was stable to bleach and modest alkaline conditions during the duration of treatment and is highly suitable for reducing damage caused by the bleaching process, which results in preserving good hair integrity.

While it is not a requirement for the bis-PCA-dimethicone molecule to be insoluble in water to prevent hair damage in bleaching tests, insolubility (even when neutralized) tends to give longer lasting deposition after rinsing. Therefore, a Y value in the above structure of 6-20 is ideally suited for this invention. Since the molecule is generally insoluble, even when neutralized, humectants, emollients and surfactants may be used as co-solvents in this composition to achieve a final composition that is stable as a solution or dispersion of the bis-PCA-dimethicone.

In accordance with another aspect of the invention, there are provided improvements in the bleaching of hair. The improved bleaching process includes first adding a heat treatment composition to a mixture of a peroxide developer and bleaching base to form an alkaline bleaching composition; applying the alkaline bleaching composition to hair to bleach the hair; allowing the alkaline bleaching composition to remain on the hair until it is sufficiently lighter in color or until color lightening process is exhausted; rinsing the hair to substantially completely remove the alkaline bleaching composition; and, optionally repeating the application and rinsing cycles up to 3 complete cycles to achieve desired lighter color. Optionally, a neutralizer conditioner solution can be applied to the hair for a time sufficient to eliminate any residual alkalinity thereafter.

In those aspects of the invention where the hair treatment compositions described herein are included with hair coloring dyes to enhance color deposition, color fastness and enhanced color vibrancy and color intensity, it is preferred that the hair treatment compositions be present in amounts of from about 0.025 to 0.25 parts for each part of permanent hair coloring dye. Examples of such enhanced hair dyeing compositions are made by combining:

a. A permanent hair color dye composition—1 part b. A developer, as to catalyze the oxidative dyeing process—1 to 2 parts to each part a)

c. Hair treatment compositions as described herein, i.e. those substantially free of maleic acid and containing from about 1% to 25% by weight of a polymer of Formula (I):

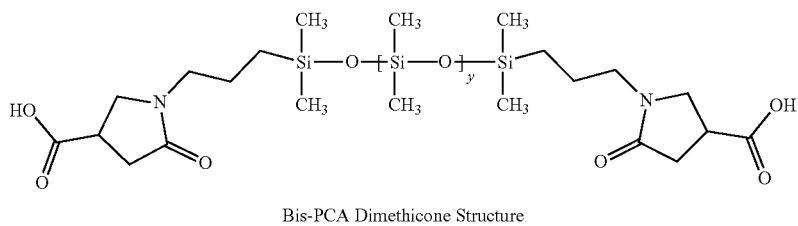

Bis-PCA Dimethicone Structure or Formula (II)

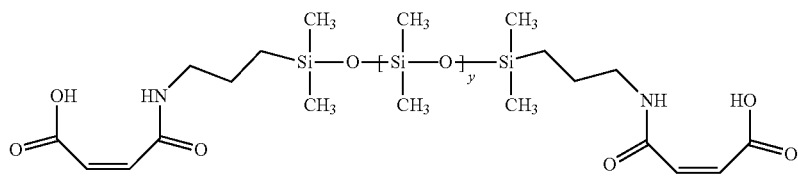

Bis-Malamic Acid Dimethicone Structure wherein y is 6 to 20;
from about 0.1 to 10% by weight of a surfactant;
from about 5 to about 30% by weight of a humectant;
a pH adjuster in an amount sufficient to bring the pH of the hair treatment composition to from about 9 to about 10; and water;
used in an amount of from about 0.025 to about 0.25 parts for each part a). After being combined as a mixture, the resulting product is applied onto hair for a period of 5-60 minutes, whereby the time is used to produce the desired shade of color in the hair. Leaving the hair color formulation in contact with hair longer progressively produces hair with more saturation.

The term "hair level" is used herein to describe how light or dark a color is regardless of its tonal character. Hair level ranges from level 1, true black, to level 10, lightest blonde/pale yellow. This is numerical system is based on international standards. More specifically, level 1 is black; level 2 is very dark brown; level 3 is dark brown; level 4 is medium brown; level 5 is light brown; level 6 is dark blonde; level 7 is medium blonde; level 8 is light blonde; level 9 is very light blonde; and level 10 is lightest blonde.

The term "hair tone" or "hair tonal character" as used herein refers to describing the shade of that hair level. Hair tone qualities can be categorized into as warm, neutral or cool. These tones can be further subdivided into Ash, Neutral, Beige, Gold, and Red. Ash can be defined as color without red or gold highlights. Neutral can be defined as tones with an equal amount of primary colors. Beige appear as warmer (pink) depending on the base in the color. Gold can be described as color that adds golden highlights/tones to hair. Red appears with color that introduces red highlights/tones to hair.

A review by Franca (Cosmetics 2015, 2, 110-126; doi: 10.3390/cosmetics2020110) teaches the primary mechanisms underpinning hair coloring systems that yield standard color depth and fastness attributes. Not being bound to theory, the current accepted mechanism of oxidative hair coloring involves three mains steps, wherein step 1, the color coupling molecules are combined with color activators and applied onto hair, step 2, the hair color formula penetrates the hair shaft to deliver the color molecules, and step 3, the color fuses within the cortex of the hair to be fade resistant. The targeted end result of this process is to yield a vibrant and long-lasting hair color. The use of oxidation conditions is taught using permanent dyes whereby the final shade of color is diffused deeper into the hair shaft and allowed to react and grow in molecular size until becoming essentially entrapped in the hair cortex. There are several conditions required to promote hair color durability, such as, but not limited to, the dye type, oxidizing agents with ammonia hydroxide, couplers, reaction modifiers and formulation vehicle (i.e. emulsion) of the oxidative dye package. Demi-Permanent dyes deposits color pigment onto the hair cuticle without penetrating it and can be used in conjunction with permanent color process.

The compositions of the present invention allow the dye and developer under alkaline conditions to have enhanced penetration and extend the reaction time to allow for more of the final shade to develop, while preventing and minimizing damage to the hair shaft.

EXAMPLES

Example 1

A bis-amino siloxane with an average Y=10 was used to prepare a bis-PCA dimethicone according to the general procedures taught in U.S. Pat. No. 5,596,061 by reacting one itaconic acid for each equivalent of amine present. The structure of this polymer is shown in FIG. 1 above. As an additional water insolubility test, the polymer when neutralized to pH 10 remained water insoluble.

Example 2

A bis-amino siloxane with an average Y=10 was used to prepare a bis-maleamic acid dimethicone by reacting one equivalent of maleic anhydride for every amino equivalent present thus ensuring there was no free maleic acid present. This polymer was made in accordance with U.S. Pat. No. 8,952,080, example 2 Preparation of Siloxane Macromer (B) and exhibited as their structure V. As an additional water insolubility test, the polymer when neutralized to pH 10 remained water insoluble.

Example 3

The following test solution was prepared as follows.

| Phase | Ingredient | Formula 3A Weight % | Formula 3B Weight % |
|---|---|---|---|
| A | Product of example 1 | 16.3 | |
| | Product of example 2 | | 16.3 |
| | Gransurf GR-50 | 5.3 | 5.3 |
| B | Water | q.s. | q.s. |
| | 1,3 Butylene Glycol | 24.4 | 24.4 |
| | AMP-95 | 3.2 | 3.2 |
| | TEA | Q.S. to pH 9.0-10.0 | Q.S. to pH 9.0-10.0 |

General procedure for both formulas:

Phase A was combined and mixed until homogenous. Phase B was combined and mixed until homogenous. Phase B was adjusted to pH 9.0-10.0.

Phase A was added to Phase B and mixed until homogenous. The specific orders of addition are not considered critical as long as the formula is combined in the end.

Example 4

Two-part commercial hair bleaching formulas were used as a bleaching base to prove the efficacy of the test formulas 3A and 3B against controls as indicated below. Test hair tresses, L'Oréal Quick Blue bleaching powder and Salon Care 40 v/v developer were obtained from Sally Beauty supply. Five virgin human black hair tresses were obtained and cut to the same weight and length.

The bleaching process was followed according to manufacturer's guidelines. The test formulas 3A, 3B, commercially available bleach damage preventing product D (Olaplex by Liqwd, a maleic acid formula with hydrophilic linker), and E (Smartbond, L'Oréal, also a maleic acid hydrophilic formula), were individually admixed with the hair bleaching formula prior to application to hair as indicated below.

Example 4A

TRESS 2: 30 g of Bleaching powder (L'Oréal Quick Blue), 60 g of developer (Salon Care 40 v/v) and 8 g of Formula 3A was combined and mixed thoroughly to form a paste.

Example 4B

TRESS 3: 30 g of Bleaching powder (L'Oréal Quick Blue), 60 g of developer (Salon Care 40 v/v) and 8 g of Formula 3B was combined and mixed thoroughly to form a paste.

Example 4C

CONTROL: TRESS 1: 30 g of Bleaching powder (L'Oréal Quick Blue), 60 g of peroxide developer (Salon Care 40 v/v) was combined and mixed thoroughly to form a paste and marked the "Control"

Example 4D

TRESS 4: 30 g of Bleaching powder (L'Oréal Quick Blue), 60 g of developer (Salon Care 40 v/v) and 8 g of commercially available bleach damage preventing product D was combined and mixed thoroughly to form a paste.

Example 4E

TRESS 4: 30 g of Bleaching powder (L'Oréal Quick Blue), 60 g of developer (Salon Care 40 v/v) and 8 g of commercially available bleach damage preventing product E was combined and mixed thoroughly to form a paste.

General bleaching process: Each bleaching processing formula indicated below was brushed onto a virgin brown hair tress and wrapped in aluminum foil and allowed to stand at ambient temperature for 1.5-2.0 hours. After the bleaching period, the tresses where rinsed with water. The bleaching step was repeated for three cycles to form a complete bleaching process.

Results

After all cycles were completed, each tress was evaluated by ease of wet/dry combing, frizziness, breakage, quality of tips, hair smoothness, shine and appearance. There was an overall significant improvement in hair tress quality for 4A and 4B (Inventive Examples) compared to 4D and 4E (commercially available bleach damage preventing products examples) and the 4C (control). Tresses treated with example formulas 3A and 3B had minimal overall breakage, significant improvement in smoothness, ease of wet/dry combing, and improved appearance. The control hair was extremely poor in appearance, had extensive hair breakage after wet/dry combing, and resulted in straw-like texture with significant damage to the tips. Commercially available bleach damage preventing products D and E were similar in performance, whereby product D was slightly better with less breakage than product E.

Overall Performance $$4A=4B>>4D>4E>>4C$$

In conclusion, the test formulas 3A and 3B, as added to a standard bleaching process clearly prevented damage above the standard of commercially available controls. The structural integrity of the treated hair tresses was reinforced compared to the control over three consecutive bleaching cycles. The dimethicone backbone is hydrophobic and yielded hair that was smooth an Chromameter as related to depth of color.

Examples 5-8

The CIELAB color space (also known as CIE L*a*b* or sometimes abbreviated as simply "Lab" color space) is a color space defined by the International Commission on Illumination (CIE) in 1976. CIE L*A*B* is also related to any instrument used to measure and quantify human color perception by outputting values in LAB color space. There are three major things necessary to quantify human color perception. They are a) a light source; b) a specimen and; c) a spectrometer. A light source normally emits white light which can be dispersed by a prism into all wavelengths of visible light. Each type of light source (i.e. daylight, incandescent, fluorescent, etc.) has a signature spectral behavior in the visible wavelength which can be characterized and standardized. Objects contain pigments or dyes that absorb some wavelengths while reflecting other wavelengths. Also, objects can modify the reflection of light to be glossy to diffuse. The amount of light transmitted can be quantified to give the object's color characteristics. The quantification of the human eye is based on observer's relative sensitivity to the spectral colors. The human eye has three types of receptors that is sensitive to red, green and blue. By adjusting the intensity of these three primary colors mixed together it is possible to encompass the entire visible spectrum. A photodetector is able to measure color to simulate the standard function of the human eye. The spectrum reflected from the specimen is measured by the intensity at each wavelength then calculated to provide the data. The CIE L*a*b* color space is a 3-dimensional rectangular color space. The 3 axes are L*(lightness) axis; a*(red-green) axis; and b*(blue-yellow) axis.

For this test, both hair samples were scanned by data color international Spectraflash 600: the control hair tress was scanned first as the standard, and the test hair tress after as the batch. This particular software uses comparing to obtain results, each result is how the batch compares to the standard. The scan takes 3 different light source and records each independently: F02 10 Deg is cool white fluorescent light at 10 degrees, A 10 Deg is incandescent light at 10 degrees and D65 10 Deg is noon daylight at 10 degrees. The values recorded are classified as the difference (Δdelta value) from one sample (or a color standard) to another sample. DL is delta L, this measurement points to the difference in lightness of the standard to the batch. Da is delta a, this measurement points to the difference in a value of color (+a is magenta). Db is delta b, this measurement points to the difference in b value of color (−b is blue). DC is delta C, this measurement points to the difference in chroma or saturation. DH is delta H, this measurement points to the difference in Hue (color spectrum). Finally, DE is delta E, this measurement points to the difference in L, a and b values together using formula $$\Delta E = \sqrt{((\Delta L)^2 + (\Delta a)^2 + (\Delta b))^2}.$$

General Permanent Hair Coloring procedure.

For all the following hair coloring examples, a large tress of virgin dark brown hair was bleached to obtain a typical hair color lift of Level 6-7. This bleached tress was used in the following Examples 5-8 whereby the original full tress was cut into a series of smaller (~1 inch wide) tresses (or test swatches) all having the same bleach level of 6-7.

The following hair coloring procedure was followed according to the manufacturer's guidelines except when an experimental component was added to the manufacturers product to demonstrate improved color saturation attributes of the invention.

Typical procedure outlined requires mixing 1 part of the hair color with 2 parts of developer. This paste is applied onto hair and allowed to remain for a time interval as specified in each example. The hair was then rinse with water, followed by shampoo and conditioner.

Control Example 5 a 1" wide test swatch of bleach lift level 6-7 was prepared by as outlined above. Applied onto this swatch was 7.5 g of Permanent gel hair color (Wella ColorCharm 7R), 15 g of developer (Salon Care 40 v/v). This paste was allowed to remain for 45 minutes. The hair was then rinse with water, followed by shampoo and conditioner.

Experimental Example 6 a 1" wide test swatch of bleach lift level 6-7 was prepared by as outlined above. Applied onto this swatch was 7.5 g of Permanent gel hair color (Wella ColorCharm, 7R), 15 g of developer (Salon Care 40 v/v), and 1 g of inventive Formula 3B. This paste was allowed to remain for 45 minutes. The hair was then rinse with water, followed by shampoo and conditioner.

After the hair color treatment, each hair tress was evaluated by visual and CIE LAB chromameter. There was an enhancement in the color deposition and quality of the hair texture on example tress 6 compared to example 5 (control). Tress 6 had more saturation with the color Red and was darker overall. Direct comparison using control Tress 5 as the standard in the CIELAB testing yields an overall Strength of about 203% for the invention example tress 6. The overall texture of the experimental tress was of smoother quality with better combability. The hair tresses were subjected to 20 shampoo cycles and example 6 exhibited significantly higher overall red color retention in after all cycles.

CIE LAB dataset: Colored Tress 6 delta values (using tress 5 as standard).

| | Strength: 202.81% | | | | | |
|---|---|---|---|---|---|---|
| | is: Darker More Red | | | | | |
| Ill/Obs | DL* | Da* | Db* | DC* | DH* | DE* |
| F02 10 Deg | −8.28 | 1.59 | −6.21 | −4.05 | −4.97 | 10.47 |
| A 10 Deg | −7.39 | 2.00 | −4.42 | −1.88 | −4.47 | 8.84 |
| D65 10 Deg | −7.5 | 2.00 | −4.79 | −1.59 | −4.94 | 9.12 |

Timed Color Saturation Study.

The following examples help illustrate the relation of time and saturation, whereby the invention is clearly shown to significantly outperform the control.

Example 7 (Control)

Same as example 5 except the hair swatch was only left in contact with the color formulation for 15 minutes.

Example 8 (Control)

Same as example 5 except contact with the color formulation was only 30 minutes.

Example 9 (Control)

Repeat of Example 5 with contact time of full 45 minutes.

Example 10 (Experimental)

Same as example 6 except the hair swatch was only left in contact with the color formulation for 15 minutes.

Example 11 (Experimental)

Same as example 6 except the hair swatch was only left in contact with the color formulation for 30 minutes.

Example 12 (Experimental)

Repeat of example 6 with contact time of full 45 minutes.

Results from Time Color Saturation Study

After the hair color treatment, each hair tress was rinsed with lukewarm water at the designated time to stop the color oxidation process and stop hair color deposition. It was clearly apparent that the texture and appearance of Tress 10, 11, and 12 where improved compared to the Tress not treated with Formula 3B. It was apparent that the hair tress treated with Formula 3B had enhanced color saturation relative to the control. The overall performance of hair color saturation is ranked in the following order:

Tresses: 12>11>9>10=8>7

This study concludes that each tress with the inventive composition significantly outperformed the related control for color deposition for each time duration tested. Furthermore, example tress 11 (with only 30 min duration) outperformed tress 9 (with a full 45 min duration).

The patents, patent applications and publications mentioned herein are incorporated herein by reference.

We claim:

1. A hair treatment composition, comprising
a) from about 1% to 25% by weight of a polymer selected from the group consisting of Formula (I):

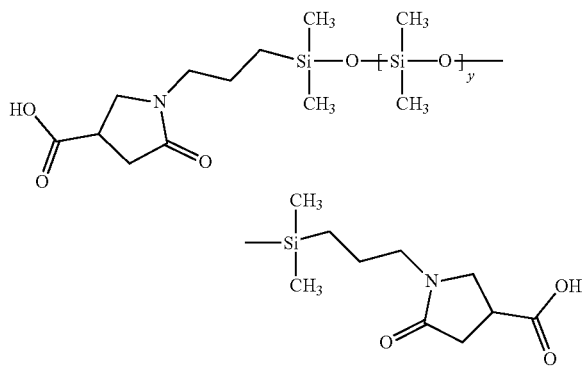

and Formula (II)

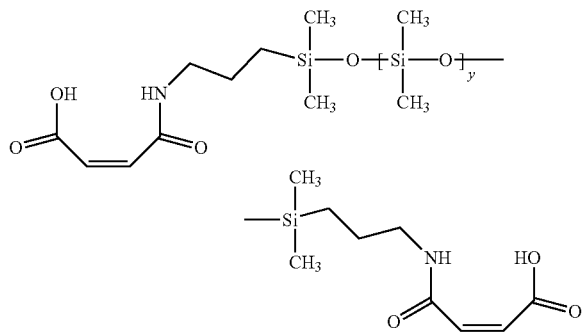

wherein y is 6 to 20;
b) from about 0.1 to 10% by weight of a surfactant;
c) from about 5 to about 30% by weight of a humectant;
d) a pH adjuster in an amount sufficient to bring the pH of the hair treatment composition to from about 9 to about 10; and
e) water;
wherein the hair treatment composition is substantially free of maleic acid.

2. The hair treatment composition of claim 1 wherein the polymer is the compound of the Formula (I).

3. The hair treatment composition of claim 1 wherein the polymer is the compound of the Formula (II).

4. The hair treatment composition of claim 1 wherein y is 8 to 12.

5. The hair treatment composition of claim 4 wherein y is 10.

6. The hair treatment composition of claim 1 wherein the surfactant is a silicone surfactant.

7. The hair treatment composition of claim 6 wherein the silicone surfactant is an alkyl dimethicone copolyol.

8. The hair treatment composition of claim 7 wherein the alkyl dimethicone copolyol is disodium PEG-12 dimethicone sulfosuccinate.

9. The hair treatment composition of claim 1 wherein the humectant is a polyhydric alcohol.

10. The hair treatment composition of claim 9 wherein the polyhydric alcohol is a polyalkylene glycol.

11. The hair treatment composition of claim 7 wherein the polyalkylene glycol is 1,3-butylene glycol.

12. The hair treatment composition of claim 1 wherein the pH adjuster is 2-amino-2-methyl-1-propanol.

13. The hair treatment composition of claim 1, further comprising including a volatile amine pH adjuster.

14. The hair treatment composition of claim 13, wherein the volatile amine is selected from the group consisting of aminomethyl propanol and triethanolamine.

15. The hair treatment composition of claim 1, wherein the amount of the polymer is from about 15 to about 20% by weight; the amount of surfactant is from about 2 to about 7% by weight; and the amount of humectant is from about 20 to about 28% by weight.

16. A hair treatment composition according to claim 1, comprising:

| INGREDIENT | Wt % |
| --- | --- |
| bis-PCA-dimethicone of Formula I or II, with y = 10 | 16.3 |
| the surfactant, disodium PEG-12 dimethicone sulfosuccinate | 5.3 |
| Water | q.s. to 100 |
| the humectant, 1,3 Butylene Glycol | 24.4 |
| the pH adjuster, 2-amino-2-methyl-1-propanol as AMP-95 and optionally, triethanolamine, the composition having a pH of from about 9.0 to about 10.0. | 3.2 |

17. The hair treatment composition of claim 1, wherein the amount of free maleic acid in the composition is less than 5% by weight.

18. The hair treatment composition of claim 17, wherein the amount of free maleic acid in the composition is less than 1% by weight.

19. The hair treatment composition of claim 17, wherein the amount of free maleic acid in the composition is less than 0.1% by weight.

20. A hair bleaching composition, comprising:
(a) from about 1.0 to about 50% by weight of the hair treatment composition of claim 1; and
(b) from about 1.0 to about 50% by weight of a mixture containing a peroxide developer and a bleaching base, wherein the alkaline bleaching composition is substantially free of maleic acid.

21. The hair bleaching composition of claim 20 wherein the peroxide developer is hydrogen peroxide.

22. The hair bleaching composition of claim 20 wherein the bleaching base comprises a mixture of ammonium persulfate and potassium persulfate.

23. The hair bleaching composition of claim 20, further comprising a permanent hair coloring dye.

24. The hair bleaching composition of claim 23, wherein the ratio of the hair treatment composition to the permanent hair coloring dye is from about 0.025 to about 0.25:1.

25. A method of bleaching hair, comprising:
(a) applying the hair bleaching composition of claim 20 to hair for a time sufficient to lighten the hair in color or until the color lightening caused by the applying of the hair bleaching composition is substantially exhausted;
(b) rinsing the hair to substantially remove the alkaline bleaching composition therefrom; and optionally
(c) repeating steps (a), (b) and (c) up to three times to achieve a desired lighter hair color.

26. The method of claim 25 further comprising applying a neutralizer conditioner solution to said hair after steps (b) or (c) for a time sufficient to substantially eliminate any residual alkalinity.

27. A method of maintaining structural integrity of hair during bleaching or dyeing of the hair, comprising applying to the hair an effective amount of a water insoluble polymer selected from the group consisting of Formula (I):

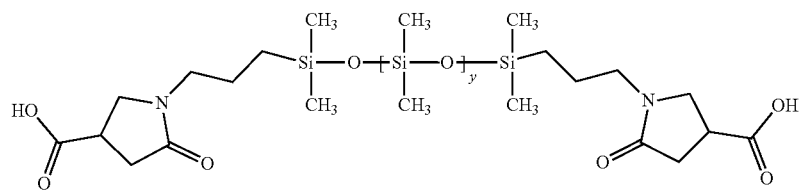

and Formula (II)

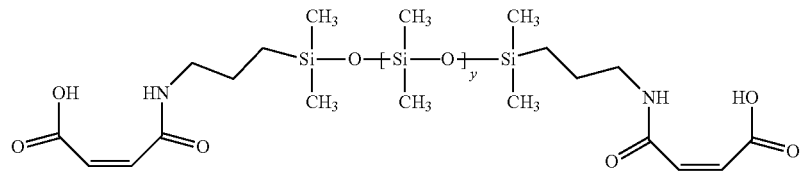

wherein y is 6 to 20; in combination with a hair bleaching agent and/or a hair coloring agent.

28. A hair treatment kit, comprising a first container comprising the composition of claim 1, a second container comprising a hair bleaching composition containing a peroxide developer and a bleaching base, and optionally a third container comprising a hair coloring dye composition.

29. The kit of claim 28, wherein the bleaching base in the form of a powder and comprises a mixture of ammonium persulfate and potassium persulfate.

30. The kit of claim 28, wherein the hair coloring dye composition further comprises an oxidizing developer and an alkalizing agent.

31. The kit of claim 30, wherein the oxidizing developer is hydrogen peroxide.

32. The kit of claim 30, wherein the alkalizing agent is ammonia or an aqueous alkali.

33. A method of oxidatively dyeing hair while at the same time avoiding damage to the hair to maintain structural integrity of keratin in the hair, which comprises the steps of:
a) applying a permanent hair color dye composition to the hair;
b) applying an oxidizing developer to the hair to catalyze the oxidative dyeing process; and
c) applying to the hair a water insoluble polymer selected from the group consisting of Formula (I):

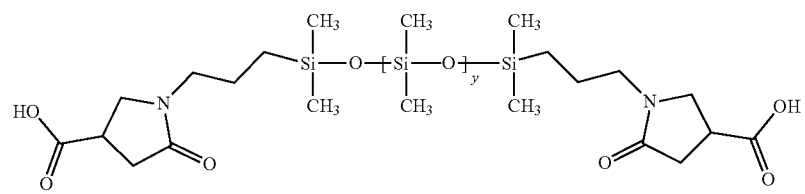

and Formula (II)

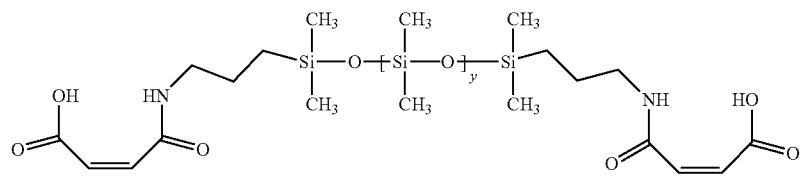

wherein y is 6 to 20;
in an amount effective to maintain the structural integrity of keratin in the hair during the oxidative hair dyeing, wherein the permanent hair color dye, the developer and the compound of the Formula (I) are each applied to the hair for from about 5 to about 60 minutes, to produce a desired shade of color in the hair, and wherein the water insoluble bis-maleamic acid dimethicone is substantially free of maleic acid.

34. The method of claim 33, wherein the permanent hair color dye composition of step (a) and the oxidizing developer applied of step (b) are first mixed together before being applied to the hair.

* * * * *